(12) United States Patent
Werner et al.

(10) Patent No.: US 6,425,863 B1
(45) Date of Patent: Jul. 30, 2002

(54) METHOD FOR MONITORING INSULIN MEDICATION

(75) Inventors: Karl Werner, Wiesloch; Peter Blasberg, Weinheim; Wilfried Muller, Konken, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/646,848

(22) PCT Filed: Mar. 26, 1999

(86) PCT No.: PCT/EP99/02074

§ 371 (c)(1),
(2), (4) Date: Feb. 28, 2001

(87) PCT Pub. No.: WO99/49777

PCT Pub. Date: Oct. 7, 1999

(30) Foreign Application Priority Data

Mar. 31, 1998 (DE) .......................................... 198 14 219

(51) Int. Cl.⁷ ............................ A61B 5/00; A61B 10/00
(52) U.S. Cl. ........................ 600/365; 128/920; 128/921
(58) Field of Search ................................. 600/365, 347, 600/316, 319, 300; 128/920, 921, 923

(56) References Cited

U.S. PATENT DOCUMENTS

| 4,282,872 A | | 8/1981 | Franetzki et al. | |
|---|---|---|---|---|
| 4,686,624 A | * | 8/1987 | Blum et al. | 128/921 |
| 4,731,726 A | * | 3/1988 | Allen, III | 600/368 |
| 5,019,974 A | * | 5/1991 | Beckers | 600/316 |
| 5,997,475 A | * | 12/1999 | Bortz | 128/920 |
| 6,269,314 B1 | * | 7/2001 | Iitawaki et al. | 128/920 |

FOREIGN PATENT DOCUMENTS

| DE | 2758467 A1 | 7/1979 | A61M/5/14 |
|---|---|---|---|
| EP | 0290683 A2 | 11/1988 | G06F/15/42 |
| EP | 0462466 A2 | 12/1991 | A61B/5/00 |
| EP | 0483595 A2 | 5/1992 | G06F/15/42 |
| GB | 2218831 A | 11/1989 | G06F/15/42 |

* cited by examiner

*Primary Examiner*—Kevin Shaver
*Assistant Examiner*—Navin Natnithithadha
(74) *Attorney, Agent, or Firm*—Richard T. Knauer; Jill L. Woodburn

(57) ABSTRACT

Method for monitoring insulin medication in which blood sugar values are determined before and after a meal. The difference between these measured values is plotted against a quotient calculated from the bread units ingested during the meal and the insulin units used to compensate for these bread units. Displaying many such points on a graph provides criteria for improving the insulin medication.

20 Claims, 2 Drawing Sheets

METHOD FOR MONITORING INSULIN MEDICATION

BACKGROUND AND SUMMARY OF THE INVENTION

The object of the present invention is to provide a diabetic or a person taking care of them with a method for adapting the insulin medication to the specific needs of the diabetic.

Instruments for measuring blood glucose are known in the prior art which have a so-called diary function. An example of such an instrument is the Accutrend DM from the Boehringer Mannheim Company. A diabetic can use this instrument to determine and store his blood glucose concentrations. The time course of the measured blood glucose values shows the patient whether his insulin therapy is suitable. The aim of the treatment is to keep the blood glucose in a normal range which is approximately between 80 and 180 mg/dl. If the blood sugar level decreases below a value of 50 mg/dl this is referred to as hypoglycaemia which is dangerous for the patient since it impairs his cognitive powers and he may even fall into a so-called hypoglycaemic shock which can lead to death. In contrast blood sugar values above 250 mg/dl are undesired since they can lead to long-term side effects such as diabetic feet or loss of sight. New types of treatment allow the patient to dose meals, insulin and physical activities according to needs. However, in order to carry them out successfully the diabetic must learn strategies for insulin treatment. The system known in the prior art already enables a patient to observe to a certain extent what influence food intake, physical activities and insulin administration has on his blood sugar level. However, the prior art systems do not provide the user with a simple method for systematically monitoring the treatment by insulin administration and to take measures to improve the therapy. The situation is made worse by the fact that the insulin sensitivity of the patient changes during the day.

Hence the object of the present invention was to provide the diabetic or a person who cares for him with a simpler method to monitor and systematise diabetic treatment. The present invention proposes a method in which blood sugar values that are determined before and after meals are compared to a quotient of insulin doses to bread units.

The present invention concerns a method for monitoring insulin medication comprising the steps a) providing sets of data containing the following data:
   a blood sugar value ($BV_i$), which was determined before a meal,
   a blood sugar value ($BN_i$), which was determined after a meal,
   the bread units ($BE_i$) which were ingested during the meal,
   the insulin units ($I_i$) which were administered between the determination of the blood sugar values $BV_i$ and $BN_i$, b) calculating blood sugar differences $\Delta B_i$ from the blood sugar values before and after the meal for the individual sets of data, c) calculating a quotient $Q_i$ from the insulin units ($I_i$) and bread units $BE_i$, d) plotting points $P_i$ ($\Delta B_i$; $Q_i$) in a system of coordinates comprising a first coordinate for the blood sugar differences ($\Delta B_i$) and a second coordinate for the quotients ($Q_i$), e) output of the coordinate system with the points on an output device.

DETAILED DESCRIPTION OF THE INVENTION

Figure 1:
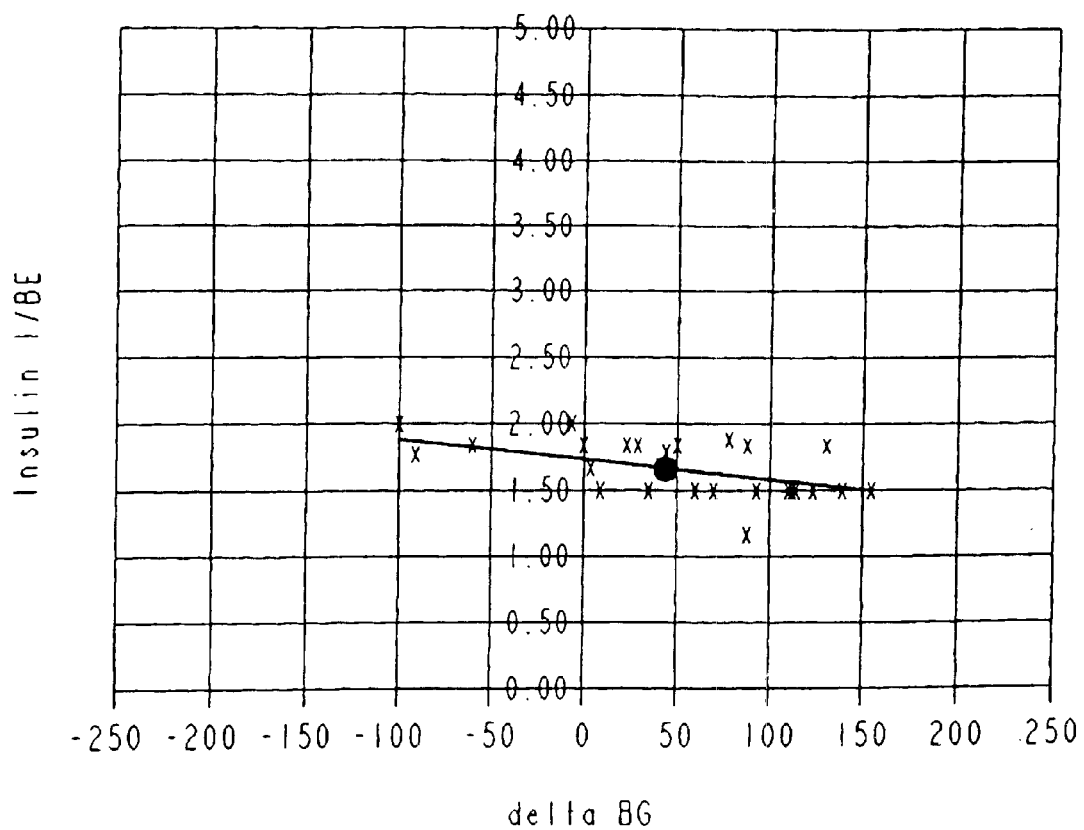
FIG. 1 illustrates the difference between the blood glucose values ($\Delta B_i = BN_i - BV_i$) plotted according to the invention against the quotients ($Q_i = I_i/BE_i$) of insulin dose and bread units.

The present invention enables the user to observe the influence of meals and insulin doses on his blood sugar level. The data used for this are the bread units of meals and the insulin units that are administered. These are the main factors which have an influence on the blood sugar level. In addition to these influencing variables, physical activities and physiological factors play a part in changing the blood glucose concentration. Sporting activities consume blood sugar and hence this effect can be taken into account by subtracting corresponding equivalents of the bread units ingested during the meal.

The bread units (BE) used in this invention are common in the prior art. For example there are tables which show how many bread units have to be estimated for a defined amount of a particular food. A diabetic can use such tables to calculate how many bread units a particular meal contains. The term bread units is also intended to encompass other units of quantity which are characteristic for the amount of carbohydrates in the food which should be degraded by the administered insulin. A calculation of bread units from the amount of ingested carbohydrates and the influence of dietary fibres, fats and protein is given in the book "Diabetologie für praktische Ärzte und Kliniker" by B. Knick and J. Knick. The corresponding passage in the 3rd revised and extended edition is in chapter 4.2.

The insulin units (I) mentioned in the invention are also well-known in the prior art. The international unit for insulin is defined for example in chapter 5.4 of the above-mentioned book "Diabetologie . . . ". However, in the present invention the term "insulin units" is not limited to international units but is used to represent units which enable the amount of insulin to be specified. Nowadays the diabetic almost exclusively uses standardized insulin in which case it is known which amount has to be injected in order to administer a desired number of insulin units. In practice the diabetic does not need to carry out such a calculation since the syringe systems for administering insulin can be set for a desired quantity of insulin which is then administered accurately and reliably. In practice there are various types of insulin which differ in their profile of action with regard to the manner in which the insulin is made available to the body. Within the sense of the invention the set of data should also contain information on the type of insulin so that the user can also find out which insulin or which combination of the available types of insulin are most suitable for him. For this purpose the points plotted in the system of coordinates can for example be labelled according to the type of insulin.

A quotient is formed from the intake of bread units and the insulin units which have been administered to compensate for the bread units. Usually the quotient is expressed as I/BE but according to the invention the reciprocal ratio can also be used. The determined quotient is preferably checked for plausibility before it is processed further in the inventive method. This for example entails checking whether the quotient is positive or whether it is within a particular range (e.g. from 0.1 to 10).

In addition to the bread unit intake and the administered quantity of insulin, the measured blood sugar concentrations or blood sugar values which were determined before and after the respective meal are also necessary for the sets of data used in the invention. The blood sugar value determined before the meal should have been measured shortly before the meal and preferably less than 1 hour before the start of the meal. Preferably only those measurements are allowed for the further evaluation in which the blood sugar value before the meal is in the normal range (80 to 180 mg/dl).

The blood sugar value after the meal should be measured at the latest before the next meal. The determination of such blood sugar values is well-known in the prior art so that it is not described in detail here. It is only pointed out that in addition to the conventional determination using capillary blood which is obtained from a finger pad, it is also possible to use other invasive and non-invasive methods for determining the blood sugar values.

In addition to the described insulin doses to compensate the bread units ingested during meals, a diabetic can also inject insulin to compensate excessively high blood sugar values (so-called correction insulin). These injections can in principle take place during the entire day. This correction insulin is not taken into consideration in the present invention if it has been administered sufficiently long before the meal and the corresponding measurement of blood sugar before the meal. In this case it can be assumed that the correction insulin has already become substantially effective and its effect on the blood sugar value after the measurement is small. However, if the correction insulin is administered together with or shortly before or after the injection before the meal then it should be taken into account when calculating the administered dose of insulin as part of the inventive method. However, as already described above only those sets of data are preferably used for the evaluation or plotting in which the blood sugar value is in the normal range before the meal.

Differences $\Delta B_i$ are calculated from the blood sugar values before ($BV_i$) and after ($BN_i$) the meal. $\Delta B_i$ is preferably $BN_i-BV_i$ but $BV_i-BN_i$ can also be used. It is important that a uniform method of subtraction is used within a plot.

The plotting is carried out according to the invention in the following manner:

Points are plotted in a two-dimensional system of coordinates in which the first coordinates are the blood sugar differences and the second coordinates are the above-mentioned quotient of insulin units and bread units. A Cartesian system of coordinates is usually used for the graph, the first axis of which for example extends from −200 to +200 mg/dl and the second axis of which preferably intersects the first axis at the origin. The second axis extends for example from 0 to 4.

A plot in such a system of coordinates results in a cloud of points whose position in the system of coordinates and scatter gives important information for the diabetic or for his attending physician. The closer together the points in the cloud of points i.e. the smaller the scatter, the more uniform is the treatment with insulin. However, this does not mean that the scheme of treatment with insulin is necessarily already optimal. If this cloud of points is at a large distance from the origin of the first coordinate (differences of the blood glucose values), this means that a scheme of treatment has been carried out in which the meal causes a shift in the glucose level. In contrast the aim of insulin treatment is to compensate for the influence of the meal on the blood sugar level as well as possible i.e. to achieve a blood sugar level which is in the normal range. With reference to the plotting according to the invention of points, this means that the first coordinates of the points should be as near as possible to the origin of the first axis.

In order to simplify the evaluation the centre of concentration of the cloud of points can be calculated and shown in the diagram with a special label. The coordinates of the centre of concentration are derived from the mean of the first coordinates of all points and the mean of the second coordinates of all points. In a well-adjusted diabetic the first coordinate (blood sugar differences) of the centre of concentration are near to zero and the scatter of the points about the centre of concentration is low.

The graph according to the invention can additionally be used to obtain a proposal to improve the insulin medication. For this purpose a regression line through the measured values is calculated and drawn in the diagram or the equation of the regression line is shown numerically. The value of the regression line at the origin of the first coordinate is determined from the equation or the diagram. The value obtained in this manner represents a factor which is referred to as sensitivity factor in the following.

The inventive graph can for example be shown on a display, monitor or printer.

Commercial insulin is labelled in such a manner that an ingested bread unit can be approximately compensated by an insulin unit (cf. chapter 5.10 of the above-mentioned book "Diabetologie . . . "). However, in practice the number of insulin units that are required to compensate for a bread unit depend on a number of influencing factors such as the type of insulin, the body weight of the person, the sensitivity of the person to insulin, time of day and other factors.

The sensitivity factor is a measure of how many units of insulin the respective diabetic should use to compensate for a certain number of bread units. Previously the sensitivity factor has been selected by the diabetic or doctor on the basis of experience for the respective person. Previously the selection of the sensitivity factor has been less systematic and was very time-consuming and thus the present invention is a major advance since the selection of the sensitivity factor can be systematised and improved.

The inventive graph can also be used and is probably in most cases even better, to derive a qualitative correction of the previous insulin medication from the graph. For this purpose the centre of concentration of the cloud of points is firstly determined and its first coordinate shows whether there is a positive or negative differential value of the blood glucose. If the first coordinate of the centre of concentration is positive then the diabetic has on average injected less insulin than was necessary to achieve the original insulin value before the meal. This results in a qualitative guidance to in future use somewhat more insulin per bread unit than previously. If the first coordinate of the centre of concentration is negative the converse is the case.

However, for the safety of the patient a change in insulin treatment should only be carried out when the scatter of the points in the diagram according to the invention is sufficiently small. In contrast if there is a relatively large scatter it can be assumed that influencing factors are present that are difficult to calculate and greatly reduce the reliability of the information. A scattering of the cloud of points can for example be caused by an erroneous or insufficiently accurate calculation of the bread units taken with the meal. This is a reason to train the patient so that he calculates the ingested bread units in a more consistent and accurate manner.

lunch (LUN) was taken. The table shows the difference value (delta BG) and the next column shows the quotients of insulin units and bread units for the breakfast between the measurements. The next to last column shows the insulin units administered to compensate for the breakfast. The last column shows the number of bread units taken at breakfast.

Data range: all available data of the patient

Name:
Time window: BRK - LUN
29 active cases

| Date | | | Time window | BG | | | insulin/BE | | |
|---|---|---|---|---|---|---|---|---|---|
| DD. | MM. | YY | HH:MM–HH:MM | BRK | LUN | delta BG | BRK | insulin | BE |
| 26. | 07. | 95 | 10:00–12:52 | 131 | 265 | 134 | 1.50 | 9.00 | 6 |
| 01. | 08. | 95 | 10:05–13:24 | 89 | 209 | 120 | 1.50 | 6.00 | 4 |
| 09. | 08. | 95 | 09:28–13:05 | 165 | 105 | −60 | 1.80 | 9.00 | 5 |
| 13. | 08. | 95 | 09:56–13:41 | 129 | 240 | 111 | 1.50 | 6.00 | 4 |
| 22. | 08. | 95 | 08:18–11:52 | 171 | 222 | 51 | 1.80 | 9.00 | 5 |
| 30. | 08. | 95 | 10:28–14:03 | 120 | 175 | 55 | 1.50 | 6.00 | 4 |
| 10. | 09. | 95 | 07:50–13:50 | 162 | 154 | −8 | 2.00 | 8.00 | 4 |
| 12. | 09. | 95 | 08:11–11:09 | 146 | 179 | 33 | 1.80 | 9.00 | 5 |
| 19. | 10. | 95 | 10:14–14:17 | 139 | 144 | 5 | 1.67 | 10.00 | 6 |
| 20. | 10. | 95 | 10:25–12:40 | 159 | 250 | 91 | 1.80 | 9.00 | 5 |
| 26. | 10. | 95 | 10:17–13:33 | 130 | 175 | 45 | 1.75 | 7.00 | 4 |
| 28. | 10. | 95 | 08:14–13:00 | 177 | 204 | 27 | 1.80 | 9.00 | 5 |
| 31. | 10. | 95 | 08:58–12:37 | 87 | 155 | 68 | 1.50 | 6.00 | 4 |
| 02. | 11. | 95 | 10:17–14:22 | 166 | 73 | −93 | 1.75 | 7.00 | 4 |
| 04. | 11. | 95 | 09:34–14:17 | 137 | 43 | −94 | 1.75 | 7.00 | 4 |
| 09. | 11. | 95 | 09:36–13:12 | 74 | 165 | 91 | 1.20 | 6.00 | 5 |
| 11. | 11. | 95 | 09:59–14:49 | 174 | 253 | 79 | 1.83 | 11.00 | 6 |
| 21. | 11. | 95 | 09:58–14:48 | 191 | 242 | 51 | 1.80 | 9.00 | 5 |
| 22. | 11. | 95 | 10:29–13:37 | 119 | 128 | 9 | 1.50 | 9.00 | 6 |
| 24. | 11. | 95 | 09:53–12:41 | 154 | 209 | 55 | 1.50 | 9.00 | 6 |
| 28. | 11. | 95 | 08:21–13:56 | 126 | 222 | 96 | 1.50 | 9.00 | 6 |
| 29. | 03. | 96 | 09:24–14:49 | 92 | 205 | 113 | 1.50 | 9.00 | 6 |
| 01. | 04. | 96 | 09:35–13:48 | 80 | 189 | 109 | 1.50 | 9.00 | 6 |
| 02. | 04. | 96 | 08:23–13:58 | 131 | 140 | 9 | 1.50 | 9.00 | 6 |
| 10. | 04. | 96 | 10:29–14:17 | 106 | 142 | 36 | 1.50 | 9.00 | 6 |
| 22. | 04. | 96 | 10:28–13:26 | 85 | 237 | 152 | 1.50 | 9.00 | 6 |
| 30. | 04. | 96 | 10:23–13:10 | 151 | 277 | 126 | 1.80 | 9.00 | 5 |
| 07. | 05. | 96 | 09:01–12:30 | 157 | 158 | 1 | 1.80 | 9.00 | 5 |
| 08. | 05. | 96 | 09:55–14:45 | 252 | 152 | −100 | 2.00 | 12.00 | 6 |

However, a strong scattering of the cloud of points can also be caused by factors which are outside the sphere of influence of the patient. For example the insulin consumption per bread unit may be subject to physiological variations. The ability to recognize the necessity for measures on the basis of the scatter is a major advantage of the invention.

The present invention is elucidated in more detail on the basis of the following examples:

Since the insulin sensitivity changes depending on the time of day, the day was divided into time windows in which the sensitivity is assumed to be substantially constant.

The following table gives an example of these time windows and their names:

| | |
|---|---|
| 4:30 to 10:30 | breakfast (BRK)–lunch |
| 10:30 to 15:00 | lunch (LUN)–dinner |
| 16:00 to 21:00 | dinner (DIN)–bed |
| 21:00 to 4:30 | bed, night (BED)–breakfast |

The following table shows measured blood glucose values which were measured before breakfast (BRK) and before The difference between the blood glucose values ($\Delta B_i = BN_i - BV_i$) was plotted according to the invention against the quotients ($Q_i = I_i/BE_i$) of insulin dose and bread units shown in FIG. 1. FIG. 1 also shows the centre of concentration (S) of the cloud of points and the regression line (R). The figure also shows that the patient has used a factor in the range 1.2 to 2.5 for many medications in order to calculate his insulin dose from the bread units. The relatively high $\Delta B_i$ range of −100 to +180 shows that the patient adheres relatively rigidly to certain insulin doses without adequately taking into account the amount of ingested bread units when choosing the insulin dose. Hence a training could be carried out as a measure to improve the control of this diabetic in which he receives information for more accurate calculation of the bread units and of the necessary amount of insulin to compensate for these bread units.

Figure 2:
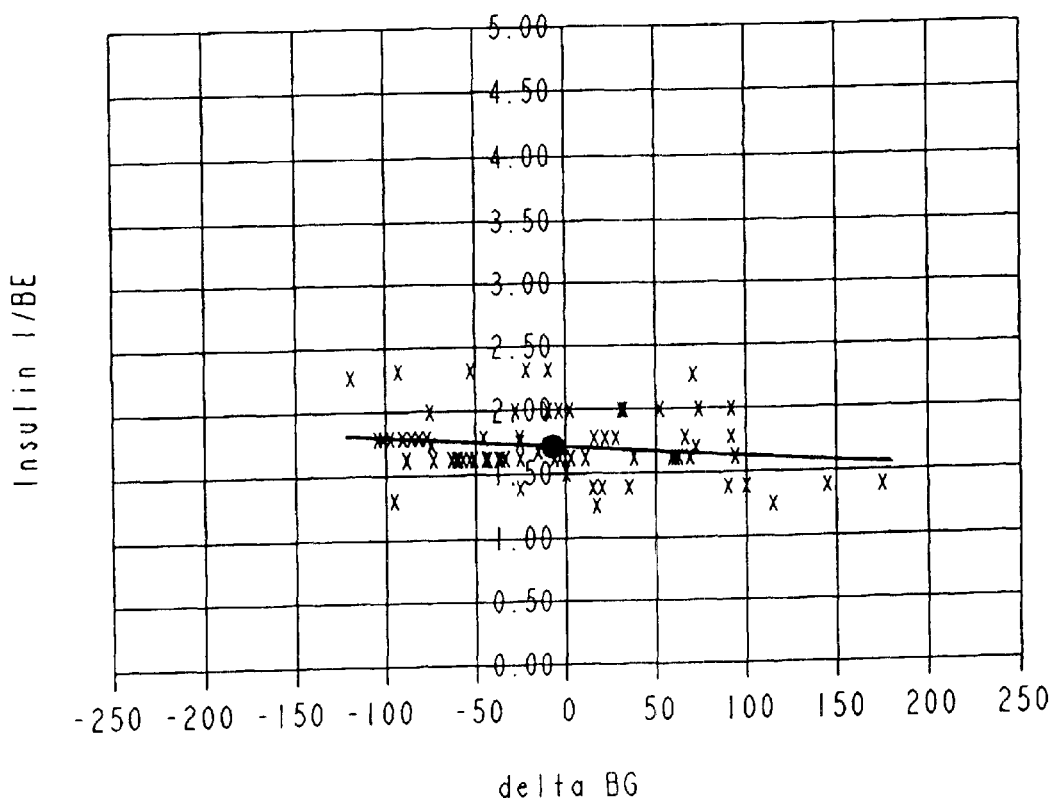
FIG. 2 shows a corresponding diagram which illustrates the compensation of breakfast by the same diabetic.

FIG. 2 shows a corresponding diagram which illustrates the compensation of breakfast by the same diabetic. It can be seen that the centre of concentration is in the region of the origin which suggests that the diabetic is quite well stabilized.

The invention additionally includes a device for carrying out the control of insulin medication. Such a device comprises an input unit which can be used by the operator to input blood sugar values before a meal, blood sugar values after a meal, bread units ingested during the meal, insulin units administered between the measurements of the blood sugar values and optionally additional data. Such an input unit is for example a keyboard. In another system described below the input unit can also be a unit to receive data transmitted from a blood sugar measuring instrument. The device also has a computing unit to calculate the blood sugar differences from the blood sugar values before and after a meal and a computing unit to calculate quotients from the bread units and the insulin units. In addition to these components, storage units to store the input data, the calculated blood sugar differences and the quotients are also required. Finally the device also comprises an output unit such as a display, monitor or printer to display the system of coordinates with points as described above whose first coordinates are the blood sugar differences and the second coordinates are the said quotients.

The present invention additionally concerns a system for monitoring insulin medication which comprises the aforementioned device and a blood sugar measuring instrument. The device and the blood sugar measuring instrument can be present separately such that the measured blood sugar values are manually transferred by the operator. However, the device and blood sugar measuring instrument are preferably coupled together by a dataline such that the values measured by the blood sugar measuring instrument can be directly transmitted to the device. In this embodiment it is advantageous if the operator can enter whether the measurement is a blood sugar value before or after the meal. Blood sugar measuring instrument and the device are advantageously accommodated together in a single housing such that the system appears to the operator as a blood sugar measuring instrument with an extended function.

What is claimed is:

1. Method for monitoring the influence of insulin medication and meals of a user, the method comprising the steps of:
    a) providing sets of data containing the following data:
        a blood sugar value (BVi) determined before the meal,
        a blood sugar value (BNi) determined after the meal,
        bread units (BEi) ingested by the user during the meal, and
        insulin units (Ii) administered to the user between the determination of the blood sugar values (BVi and BNi),
    b) calculating blood sugar differences $\Delta Bi$ from the blood sugar values (BVi and BNi) before and after the meal respectively for individual sets of data,
    c) calculating a quotient Qi from the insulin units (Ii) and bread units (BEi),
    d) plotting points Pi ($\Delta Bi$; Qi) in a system of coordinates comprising a first coordinate for the blood sugar differences ($\Delta Bi$) and a second coordinate for the quotients (Qi),
    e) outputting the coordinate system with the points (Pi) on an output device.

2. Method as claimed in claim 1, in which the blood sugar difference is calculated by an equation $\Delta Bi=BNi-BVi$.

3. Method as claimed in claim 1, in which the quotient (Qi) is calculated by an equation $Qi=Ii/BEi$.

4. Method as claimed in claim 1, in which all blood sugar values BVi and BNi are determined before or after the same type of meal.

5. Method as claimed in claim 2, in which the meal is a type of meal selected from the group of breakfast, lunch and dinner.

6. Method as claimed in claim 1, in which the blood sugar values BVi are determined no more than 1 hour before the start of the meal and the blood sugar values BNi are determined at the latest before the next meal of the user.

7. Method as claimed in claim 1, wherein the output step includes displaying a specially labelled centre of concentration with the system of coordinates on the output device.

8. Method as claimed in claim 1 or 7, further comprising the step of determining a regression line from the points (Pi).

9. Method as claimed in claim 8, wherein the output step includes displaying the regression line together with the points (Pi) and the system of coordinates on the output device.

10. Method as claimed in claim 8, wherein the output step includes displaying the value of the regression line for $\Delta Bi=0$ either graphically or numerically.

11. Method as claimed in claim 7, in which the first coordinates of the centre of concentration is shown qualitatively or quantitatively.

12. Method as claimed in claim 1, further comprising the step of checking whether the quotient (Qi) is positive and the plotting step includes selecting only sets of data for which the quotient (Qi) is positive.

13. Method as claimed in claim 1, further comprising the step of checking whether the quotient (Qi) is in the range of 0.1 to 10 and the plotting step includes selecting only sets of data are used for which this applies.

14. Method as claimed in claim 1, further comprising the step of checking whether the blood sugar value before the meal (BVi) is in the range of 80 to 180 mg/dl and the plotting step includes selecting only sets of data are used for which this applies.

15. Method as claimed in claim 1, further comprising the step of checking whether the blood sugar value before the meal (BVi) is in the range of 80 to 180 mg/dl and the quotient (Qi) is in the range of 0.1 to 10 and only sets of data are used for which this applies.

16. Device for monitoring the influence of insulin medication and meals of a user, the device comprising:
    an input unit formed to receive sets of data containing
        blood sugar values (BVi) determined before the meal,
        blood sugar values (BNi) determined after the meal,
        bread units (BEi) ingested during the meal,
        insulin units (Ii) administered between the determination of the blood sugar values BVi and BNi,
    a unit for calculating blood sugar differences $\Delta Bi$ from the blood sugar values (BVi) and (BNi) before and after the meal respectively for individual sets of data,
    a unit for calculating quotients (Qi) from insulin units (Ii) and bread units (BEi),
    an output unit formed to display a graph of ($\Delta Bi$; Qi) in a system of coordinates in which the first coordinates are the blood sugar differences ($\Delta Bi$) and the second coordinates are the quotients (Qi).

17. System for monitoring insulin medication comprising a device as claimed in claim 16 and a blood sugar measuring instrument.

18. System as claimed in claim 17, in which the device and the blood sugar measuring instrument are coupled together by a dataline such that the blood sugar measuring instrument can transmit blood sugar values to the device.

19. System as claimed in claim 18, in which the device and the blood sugar measuring instrument are accommodated in a common housing.

20. A device formed to monitor insulin medication as it relates to meals consumed by a user, the device comprising:

an input unit formed to receive data comprising blood sugar values (BVi) determined before the meal, blood sugar values (BNi) determined after the meal, bread units (BEi) ingested during the meal, and insulin units (Ii) administered between the determination of the blood sugar values (BVi) and (BNi), a unit formed to calculate blood sugar differences ($\Delta$Bi) by an equation $\Delta$Bi=BNi−BVi for individual sets of data, a unit formed to calculate quotients (Qi) by an equation Qi=Ii/BEi, and an output unit formed to display a system of coordinates in which the first coordinates are the blood sugar differences ($\Delta$Bi) and the second coordinates are the quotients (Qi).

* * * * *